United States Patent [19]
Baker et al.

[11] Patent Number: 4,894,219
[45] Date of Patent: Jan. 16, 1990

[54] BETA-AGONIST CARBOSTYRIL DERIVATIVES, ASSAY METHOD AND PHARMACOLOGICAL COMPOSITION

[75] Inventors: Stephen P. Baker, Gainesville, Fla.; Josef Pitha, Baltimore, Md.

[73] Assignee: University of Florida, Gainesville, Fla.

[21] Appl. No.: 174,874

[22] Filed: Mar. 29, 1988

[51] Int. Cl.⁴ ..................... A61K 49/00; A61K 31/47; C07D 215/20
[52] U.S. Cl. ...................... 424/9; 546/157; 514/312; 424/11
[58] Field of Search .................. 546/157; 514/312; 424/9

[56] References Cited
U.S. PATENT DOCUMENTS
4,223,137 9/1980 Yoshizaki et al. ............. 546/157 X
4,687,776 8/1987 Chow et al. ................... 546/157 X

FOREIGN PATENT DOCUMENTS
0111078 9/1978 Japan ................................. 546/157
0093053 5/1984 Japan ................................. 546/157

OTHER PUBLICATIONS
Milecki et al., "Carbostyril Derivatives Having Potent B-Adrenergic Agonist Properties", J. Med. Chem., 30, 9/1987, pp. 1563-1566.

Primary Examiner—John S. Maples
Attorney, Agent, or Firm—Dennis P. Clarke

[57] ABSTRACT

Beta-agonist carbostyril derivatives having the formula

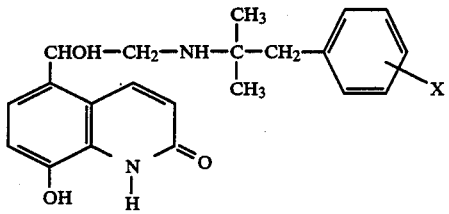

wherein X may be the ortho, meta or para position and is selected from the group consisting of halogen, amino and substituted and unsubstituted lower alkanoylamino having from 1 to 6 carbon atoms and pharmaceutically acceptable salts and complexes thereof.

9 Claims, 3 Drawing Sheets

BETA-AGONIST CARBOSTYRIL DERIVATIVES, ASSAY METHOD AND PHARMACOLOGICAL COMPOSITION

BACKGROUND OF THE INVENTION

1. Field of the Invention

The present invention relates to beta-adrenergic receptor agonists and assay methods and compositions.

2. Description of the Prior Art

Beta-adrenergic receptors are widely distributed throughout the body and mediate a variety of important physiological responses. Under normal conditions, these receptors are activated by the naturally occurring catecholamines norepinephrine, released from adrenergic nerves and epinephrine which is released from the adrenal gland. Epinephrine and several synthetic beta-agonists are presently used clinically.

The beta-adrenergic receptor appears to exist in 2 subtypes, the distribution of which varies from tissue to tissue. For example, beta-1 receptors are located in the heart whereas beta-2-receptors are located on pulmonary and vascular smooth muscle. This discovery has lead to the introduction of a number of clinically useful beta-agonists and antagonists selective for one of the subtypes.

Over the past few years, a major effort has been underway in the study of adrenergic receptors. Areas of focus have included beta-receptor regulation, mechanism of receptor coupling to cellular or tissue responses, receptor desensitization and receptor turnover [Stiles et al, *Physiol. Rev.*, Vol. 64, pp. 661-743 (1984); Maisel et al, *Biochem. Pharmacol.*, Vol. 36, pp. 1-6 (1987)]. These studies have been made possible due to the development of radiolabeled, potent and reversible beta-receptor antagonists for directly measuring the receptor. More recently, there have been developed some irreversible beta-receptor antagonists to probe the receptor both in vitro and in vivo [Atlas et al, *Proc. Natl. Acad. Sci., U.S.A.*, Vol. 73, pp. 1921-1925 (1976); Baker et al, *J. Pharmacol. Exp. Ther.*, Vol. 220, pp. 247-251 (1982); Homburger et al, *Arch. Pharmacol.*, Vol. 328, pp. 279-286 (1985)]. However, it is well known that beta-agonists induce receptor alterations related to their ability to produce responses, which antagonists do not [Abramson et al, *Biochem. Pharmacol.*, Vol. 33, pp. 869-875 (1984)]. Thus, a major research focus has been to investigate the interaction of agonists with the receptor. To date, most agonist-receptor interaction studies have been performed indirectly by competing unlabeled agonists for labeled antagonists. Although several catecholamines have been radiolabeled for direct receptor assays [Lefkowitz et al, *Proc. Natl. Acad. Sci. U.S.A.* Vol. 74, pp. 515-519 (1974); Heidenreich et al, *J. Cyclic Nucleotide Res.*, Vol. 6, pp. 217-230 (1980); Giudicelli et al, *Biochim. Biophys. Acta.*, Vol. 715, pp. 105-115 (1982)], these compounds are limited by their low specific radioactivities and instability.

In general, catecholamine beta-agonists are unstable (due to oxidation), have relatively low potency (as compared to antagonists) and can be radiolabeled to only low specific activities. These are also problems for many of the synthetic beta-agonists. Furthermore, the catecholamine agonists have drawbacks in the clinical situation due to instability, short duration of action and many potential side effects due to a lack of receptor specificity. There exists a need for beta-agonists that are stable, potent, capable of being radiolabeled and which have a long duration of action which is based on irreversible attachment to the receptor. Carbostyril congeners have been shown to have a high bio-potency for beta-adrenergic receptors [Yoshizaka et al, *J. Med. Chem.*, Vol. 19, pp. 1138-1142 (1976)]. One of these derivatives, erythro-5-(1-hydroxy-2-isopropylaminobutyl)-8-hydroxycarbostyril (procaterol) has been shown to be a potent beta-2 agonist and a bronchodilator although it suffers from one or more of the disadvantages discussed above [Yoshizaki et al, *J. Med. Chem.*, Vol. 20, pp. 1103-1104 (1977)]

Catecholamine cogeners from the class of carbostyrils, indole-2-carboxylic acid and catecholamines carrying amido groups have great biopotency. See Yoshizaki et al, *J. Med. Chem.*, Vol. 19, p. 1138 (1976); Yoshizaki et al, *J. Med. Chem.*, Vol. 20, p. 1103 (1977); Tamura et al, *J. Med. Chem.*, Vol. 24, p. 634 (1981); Albrecht et al, *Eur. J. Med. Chem.*, Vol. 20, p. 57 (1985) and Jacobson et al, *J. Med. Chem.*, Vol. 26, p. 492 (1983)].

The chemistry of compounds of this class has received some additional recent attention. See Kaiser et al, *J. Med. Chem.*, Vol. 18, p. 1803 (1985) and Amlaiky et al, *Eur. J. Med. Chem.*, Vol. 19, p. 341 (1984). Substituents on the amino group comprising the alkyl-aromatic part of an anorexic phentermine, 1-phenyl-2-amino-2-methylpropane, has been proven effective in catecholamine derivatives and β-blockers. See Moed et al, *Recl. Trav. Chim. Pays-Bas*, Vol. 74, p. 919 (1955) and Lavin et al, *J. Biol. Chem.*, Vol. 286, p. 11944 (1981).

It is an object of the invention to provide novel, stable, potent reversible and irreversible beta-adrenergic receptor agonists which will be useful as analytical probes for studying the beta-adrenergic receptor system and as drugs acting through this system.

SUMMARY OF THE INVENTION

The above and other objects are realized by the present invention which provides a compound having beta-adrenergic receptor agonist properties having the formula:

wherein X may be the ortho, meta or para position and is selected from the group consisting of halogen, amino and substituted and unsubstituted lower alkaanoylamino having from 1 to 6 carbon atoms wherein the substituents are pharmaceutically acceptable and and pharmaceutically acceptable salts and complexes thereof.

A further embodiment of the invention relates to an improved method of measuring beta-adrenergic receptors comprising exposing the receptors to a beta-adrenergic agonist and assaying the extent of interaction therebetween wherein the improvement comprises exposing the receptors to a compound, salt or complex as described above.

A still further embodiment of the invention relates to a pharmaceutical composition in unit dosage form adapted for measuring beta-adrenergic receptors comprising an amount of a compound, salt or complex described above sufficient to assayably interact with the beta-adrenergic receptors and a pharmaceutically acceptable carrier therefor.

DETAILED DESCRIPTION OF THE INVENTION

The above compounds are stable, highly potent and efficacious beta-adrenergic receptor agonists. In addition, the structure wherein X is NHCOCH$_2$Br appears to bind irreversibly to the receptor and produce irreversible agonist effects. Also, this structure shows a high degree of beta-2-receptor selectivity in vivo. These compounds are useful receptor probes for basic assays of the receptors.

Salts of the above described compounds with pharmaceutically acceptable acids, may also be employed in the assays or studies, e.g., hydrohalides such as hydrochlorides, hydrobromides, etc., acetates, maleates, benzoates, hemisulfates, fumarates, oxalates, etc.

It is preferred to employ assayable ligand-, e.g., radiolabeled compounds, salts or complexes according to the invention. Suitable radio-ligands include radioiodides, e.g., [$^{125}$I], [$^{131}$I], etc., tritium [$^3$H], etc.

Figure 1:
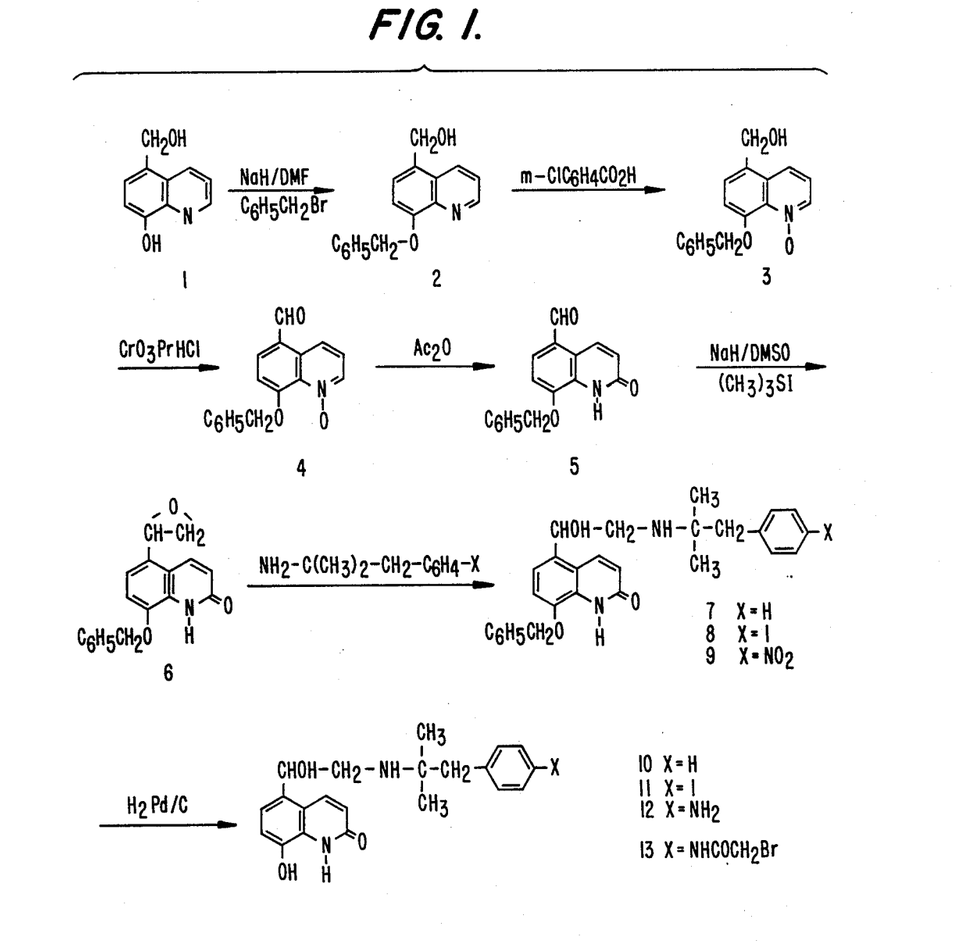

The compounds of the present invention may be prepared according to the reaction schemes set forth in FIG. 1.

The compounds, salts and complexes of the invention may be compounded with suitable pharmaceutically acceptable carriers for use in assay procedures. Suitable such carriers include cyclodextrin complexes, cellulose, sugars, e.g., saccharose.

The composition according to the present invention should contain an amount of the compound, salt or complex in unit dosage, assayable form, preferably from about $10^{-10}$ M to about $10^{-5}$ M.

The invention is illustrated by the following non-limiting examples.

EXAMPLES

Melting points in the folowing examples were determined on a hot-stage melting point apparatus (Fisher-Johns) and were not corrected. Precoated silica gel sheets (60F-254, 0.2 mm) were used for thin-layer chromatography. Silica gel (grade 60, 230–400 mesh) was used for short-column chromatography. Hydrogenations were performed in a low-pressure hydrogenator at room temperature. The compounds prepared in the following examples are numbered according to the reaction scheme set forth in FIG. 1.

5-(Hydrozymethyl)-8-hydroxyquinoline (1). 5-(Chloromethyl-8-hydroxyquinoline was prepared and converted into 5-(hydroxymethyl)-8-hydroxyquinoline (1) as described by Burckhalter et al, J. Org. Chem., Vol. 26, p. 4078 (1961): R$_f$ 0.28 (chloroformmethanol, 9:1).

8-(Benzyloxy)-5-(hydroxymethyl)quinoline (2). 5-(Hydroxymethyl)-8-hydroxyquinoline (1) (6.44 g, 36.75 mmol) was dissolved in dry dimethylformamide (40 ml) and sodium hydride (1.3 g of 80% suspension in mineral oil, corresponding to 1.04 g, 43.3 mmol) was added. The mixture was stirred until hydrogen evolution ceased (~45 min). Benzyl bromide (4.5 ml, 6.47 g, 37.8 mmol) was added and the mixture was stirred for 4 h. The solution was poured into water (350 ml) and stirred for 20 min, and the precipitate was filtered and washed with water. After crystallization from benzene, 5.4 g of product (2) was obtained; mp 192°–194° C. An analytical sample was recrystallized from toluene; R$_f$ 0.68 (chloroform-methanol, 9:1).

8-(Benzyloxy)-5-(hydroxymethyl)quinoline N-oxide (3). 8-(Benzyloxy)-5-(hydroxymethyl)quinoline (2) (5.37 g, 20.24 mmol) was suspended in methylene chloride (500 ml). m-Chloroperbenzoic acid (7 g of 85% preparation, corresponding to 34 mmol) was added and the mixture was stirred at room temperature. After 10 min the solution turned dark blue and then almost black. After 1.5 h the color began to fade and after 4 h, when no starting material could be detected by TLC, the solution turned light green. The reaction material was then extracted with aqueous sodium bicarbonate and the organic phase was separated and evaporated. The residue was stirred with acetone (150 mL) and after 30 min the product was filtered (3.45 g). The filtrate was evaporated and the residue again treated with acetone (30 ml), giving another crop of crystals (0.5 g). The product (3) has the following: mp 155°–161° C. dec; R$_f$ 0.44 (chloroform-methanol, 9:1).

8-(Benzyloxy)quinoline-5-carboxaldehyde N-Oxide (4). 8-(Benzyloxy)-5-(hydroxymethyl)quinoline N-oxide (3) (0.5 g, 1.78 mmol) was added to a solution of pyridinium chlorochromate (0.42 g, 1.95 mmol) in methylene chloride (10 ml) and the solution was stirred for 1 h, then TLC indicated that the reaction was completed. The solution was then washed with water, dried over Na$_2$SO$_4$, and evaporated. The residue was passed through a short silica gel column using dichloromethane-methanol mixture (100:3) to elute the product. Evaporation gave a yellow solid (4) (0.27 g, 55%): mp 118°–121° C.; R$_f$ 0.64 (chloroform-methanol, 9:1).

8-Benzyloxy)carbostyril-5-carboxaldehyde (5). 8-(Benzyloxy)-5-(hydroxymethyl)quinoline-5-carboxaldehyde N-oxide (4) (2.52 g, 9.02 mmol) in acetic anhydride (6 ml) was heated to 50° C. for 2.5 h. The solution was cooled, diluted with methanol (25 ml), and poured into diluted ammonia (1:10, 100 ml). After 5 min. of stirring, the mixture was extracted with methylene chloride (2×75 ml), the extracts were dried with Na$_2$SO$_4$ and evaporated, and the residue was separated on silica gel column (40 g), eluting with chloroform-methanol (99:1). The product (5) was obtained as yellow crystals (1.98 g): mp 147°–149° C.; R$_f$ 0.9 (chloroform-methanol, 9:1), 0.43 (chloroform-methanol, 19:1).

8-(Benzyloxy)-5-oxiranycarbostyril (6). Sodium hydride (0.14 g of 80% suspension in mineral oil, corresponding to 0.112 g, 4.65 mmol of hydride) was placed in a flask equipped with a magnetic stirrer, a pressure-equalizing dropping funnel, and a rubber septum with a gas-escape port. Rigorously dry reaction conditions were maintained. Argon was introduced via a hypodermic needle placed in a septum and dry dimethyl sulfoxide (6 ml) was introduced through another needle. With stirring, the flask was immersed into a 70° C. bath for 1 h. Then the solution was cooled, tetrahydrofuran (19 ml) was added, and the flask was immersed in an ice bath. A solution of trimethylsulfonium iodide (0.955 g, 4.68 mmol) in dimethyl sulfoxide (8 ml) was added dropwise during a 10 min period and the reaction was allowed to proceed for 15 min. Next a solution of 8-(benzyloxy)carbostyril-5-carboxyaldehyde (5) 0.585 g, 2.09 mmol) in dimethyl sulfoxide-tetrahydrofuran (1:1, 14 ml) was added dropwise and the brown solution was stirred for 15 min. Then the contents of the flask were poured into water (150 ml) and extracted with dichloromethane (3×50 ml). The combined extracts were washed with aqueous NaCl, dried (Na$_2$SO$_4$), and evaporated. The residue was recrystallized from benzene-isooctane (2:3), giving shiny yellowish crystals of (6) (0.49 g): mp 114°–116° C.; R$_f$ 0.38 (chloroform-ethyl-acetate, 5:3).

8-(Benzyloxy)-5-[2-[(1-phenyl-2-methylprop-2-yl)-amino]-1-hydroxyethyl]carbostyril (7). The oxirane (6) (40 mg, 0.136 mmol) and 2-amino-2-methyl-1-phenylpropane (free base of commercial phentermine) 100 mg, 0.67 mmol) were heated under reflux in 2-propanol (2 ml) for 24 h. The solvent was evaporated and the residue was dissolved in chloroform (0.5 ml) and chromatographed on a silica gel column eluted with chloroform-methanol-concentrated ammonia (96.4:0.1). The product (7), still slightly contaminated with the starting amine, was obtained as a yellow foam (40 mg): R$_f$ 0.92 (chloroform-methanol-concentrated ammonia, 4:1:0.05).

8-Hydroxy-5-[2-[(1-phenyl-2-methylprop-2-yl)amino]-1-hydroxyethyl]carbosytril (10). Crude benzyloxy derivative (7) from the previous reaction (40 mg, 0.09 mmol) was dissolved in methanol (2.5 ml) and ammonium formate (30 mg, 0.47 mmol) was added. After 5 min of stirring, palladium on carbon (10%, 20 mg) was added. The mixture was stirred for 15 min at room temperature and then 1 h at 50° C. at which time TLC indicated completion. Product (10): R$_f$ 0.37, chloroform-methanol-concentrated ammonia, 4:1:0.05; identical with the compound prepared according to Yoshizaki et al, J. Med. Chem., Vol. 20, p. 1103 (1977), isolated by silica gel column chromatography.

2-Amino-2-methyl-1-(4-nitrophenyl) propane Sulfate. A slight modification in the procedure described previously [Lavin et al, J. Biol. Chem., Vol. 256, p. 11944 (1981)] enables direct isolation of the product instead of column chromatographic separation of ortho (20%) and para (80%) isomers, both of which are products of the nitration. 2-Amino-2-methyl-1-phenylpropane hydrochloride (97 g, 0.41 mol) was dissolved in concentrated H$_2$SO$_4$ (195 ml) and the solution was cooled in an ice bath. Nitric acid (70%, 40 ml, 56 g, 0.6 mol) was added with stirring while the temperature was kept under 10° C. and then the solution was stirred for an additional 20 min. Next the mixture was poured on ice (4 l), and after 16 h white crystals were filtered, washed with cold water and methanol, and dried in air. Yield: 71.3 g (56%); mp 293°–298° C. dec; R$_f$ 0.24 (dichloro-methane-methanol-ammonia, 4:1:0.03).

2-Amino-2-methyl-1-(4-aminopenyl) propane. 2-Amino-2-methyl-1-(4-nitrophenyl)propane sulfate (6.07 g, 25 mmol) was suspended in ethanol (33 ml, 50 mmol) was added with stirring. Hydrazine (2.5 g, 78 mmol) was added, followed by Raney nickel (0.2 ml of 50% slurry). After 1 min gas evolution began, and the mixture turned yellow and was warmed to about 40° C. After 20 min gas evolution has almost ceased. Fresh catalyst was added and the mixture was boiled with stirring for 5 min to decompose excess hydrazine. After cooling, the suspension was filtered, the catalyst was washed with ethanol, and the filtrates were evaporated. The residue was extracted with diethyl ether (3×40 ml), and the extracts were dried (K$_2$CO$_3$) and evaporated, leaving a yellow oil, which solidified (3.87 g); mp 82–84° C.

2-Amino-2-methyl-1-(4-iodophenyl)propane. 2-Amino-2-methyl-1-(4-aminophenyl)propane (0.72 g, 4.33 mmol) was stirred with 5% H$_2$SO$_4$ (35 ml) and cooled to 0° C. Sodium nitrite (0.38 g, 5.5 mmol) was added to the fine suspension of sulfate in water (1 ml) while the temperature was held under 5° C. The mixture was stirred for 30 min. A clear solution formed after about 10 min. Sodium iodide (7 g, 46.7 mmol) in water (5 ml) was added and the mixture was stirred for 30 min. A dark brown solution was made alkaline with Na$_2$CO$_3$ and extracted with ether (3×25 ml). The combined extracts were washed with 10% sodium thiosulfate, dried (Na$_2$SO$_4$), and evaporated. A yellow oil was separated on a silica gel column using chloroform-methanol (96:4). The product was obtained as a yellow oil (0.41 g); R$_f$ 0.36 (chloroform-methanol, 9:1).

5-[2-[[1-(4-Iodophenyl)-2-methylprop-2-yl]amino]-1-hydroxyethyl]-8-hydroxycarbostyril (11). Oxirane 6 (0.2 g, 0.68 mmol) and 2-amino-2-methyl-1-(4-iodophenyl)propane (0.21 g, 0.76f3 mmol) in 1-butanol (4 ml) were heated under reflux for 24 h. The solvent was evaporated under reduced pressure and the remaining clear oil was separated on a silica gel column (20 g) using chloroform-methanol (97:3) as an eluent. Compound (8) was obtained in the form of a cream-colored foam (0.132 g, 35%); R$_f$ 0.27 (chloroform-methanol 9:1).

Compound (8) (0.033 g, 0.058 mmol) was dissolved in methanol (2 ml), palladium on carbon (5%, 0.05 g) was added, and the mixture was hydrogenated at 50 psi for 5 h. Then the mixture was filtered and washed with methanol (15 ml), and the filtrates were acidified with methanolic HCl (1%, 0.5 ml) and evaporated, yielding (11) as a yellow amorphous solid (0.023 g, 76%): TLC R$_f$ 0.62 (chloroform-methanol-concentrated ammonia, 4:1:0.03).

8-(Benxyloxy)-5-[2-[[1-(4-nitrophenyl)-2-methylprop-2-yl]amino]-1-hydroxyethyl]carbostyril (9). The oxirane 6 (275 mg, 0.04 mmol) and 2-amino-2-methyl-1-(4-nitrophenyl)propane (0.3 ml, 1.6 mmol) were heated in 1-butanol (3 ml) under reflux for 20 h. The solvent was evaporated and the residue was dissolved in methylene chloride (30 ml) and washed with hydrochloric acid (1%, 20 ml). Then the residue was washed with water, dried (Na$_2$SO$_4$), and evaporated. The residue was chromatographed on a silica gel column (10 g) using chloroform-methanol (97:3) as an eluent, giving 245 mg of product (9) in the form of a yellow foam: R$_f$ 0.92 (chloroform-methanol-ammonia, 4:1:03).

5-[2-[[3-[4-(Bromoacetamido(phenyl]-2-methylprop-2-yl]amino]-1-hydroxyethyl]-8-hydroxycarbostyril (13). The nitro derivative (9) (0.18 g) was dissolved in methanol (30 ml), palladium on carbon (5%, 100 mg) was added, and the mixture was hydrogenated (25 psi). The reaction was monitored by TLC (chloroform-methanol-ammonia, 4:1:0.04). The starting material (R$_f$ 0.9) disappeared after about 35 min., giving rise to two other compounds of R$_f$ 0.6 (presumably a hydroxy nitro derivative) and R$_f$ 0.17 (the desired hydroxy amino derivative). When hydrogenolysis was carried out longer, a byproduct of high R$_f$ (0.95) started to form; after 2 h it amounted to about 20%. Optimal hydrogenolysis time was 75 min, but reaction preferably should be monitored. The catalyst was filtered off, the product was washed with methanol, and the solutions were evaporated. The residue was dissolved in chloroform-methanol (3:1) and chromatographed on a silica gel column (chloroform-methanol, 7:2). Fractions containing the product were pooled, evaporated, dissolved in methanol (20 ml), and centrifuged to remove colloidal silica gel from chromatography. After evaporation and coevaporation with 2-propanol, the product 12 was obtained as a light yellow powder. Yield: 33 mg of pure product and 35 mg of slightly contaminated product; $R_f$ 0.11 (chloroform-methanol-concentrated ammonia, 4:1:0.03).

Free amine (12) (obtained by hydrogenation of 83 mg of compound (9) and used without purification, 0.17 mmol) was dissolved in dimethylformamide (2 ml). The solution was cooled in an ice bath and bromoacetyl bromide (39 mg, 0.19 mmol) was added. After 1.5 h the mixture was added dropwise to diethyl ether (100 ml) with vigorous stirring. After 5 min the precipitate was filtered and washed with ether. On exposure to air the solid quickly liquified to a viscous oil, which was again dissolved in methanol (0.2 ml), methylene chloride (0.8 ml) was added, and the resulting suspension was applied to a silica gel column (10 g). It was eluted with dichlormethane-methanol (9:1, 100 ml) and then with a 5:1 mixture. Fractions of 40 ml were collected; the product was contained in the 9th and 10th fractions. After evaporation and trituration with isooctane, these fractions gave a light yellow solid (45 mg; 46% yield) $R_f$ 0.29 (chloroform-methanol-concentrated ammonia, 4:1:0.03).

EXAMPLE 2

The biological properties of the compounds of the invention were evaluated as follows:

Biochemical Methods. Adenylate Cyclase Activity. Rat reticulocytes were induced and membranes prepared as described by Baker et al, *J. Biol. Chem.*, Vol. 260, p. 15820 (1985). Enzyme activity was determined by incubation in a total volumn of 0.1 ml containing 50 mM Tris.HCl buffer at pH 7.4, membrane protein (0.01–0.05 mg), 1.6 mM ATP, 5 mM $MgCl_2$, 1 mM EGTA, 10 mM theophylline, 0.01% bovine serum albumin, 10 units of creatine phosphokinase, and 2.5 mM phosphocreatine for 10 min at 32° C. These are the basal conditions. When stimulation of activity was measured, the assay also contained 0.5 mM GTP and varying concentrations of (−)-isoproterenol or the carbostyril derivatives. At the end of the incubation, 0.3 ml of 10 mM Tris.HCl buffer at pH 7.0 containing 5 mM EDTA was added to each tube and the tubes were placed in a boiling water bath for 5 min. After cooling to room temperature, the tubes were centrifuged for 5 min at 10000 g and the supernatant saved. The cAMP content of the supernatant was determined by a competitive protein binding assay. The amount of cAMP present was calculated from a standard curve determined with unlabeled cAMP. Enzyme activity was linear with time and protein through 10 min and 0.1 mg, respectively. Basal and GTP-stimulated activity values were substracted from the values obtained in the presence of ligands and the concentration of ligands that produced half-maximal activity ($EC_{50}$) were determined by using a dose-effect analysis with an Apple IIe computer. Membrane protein content was determined by the Lowry method with bovine serum albumin as standard.

β-Adrenergic Receptor Binding. The ability of (−)-isoproterenol and the carbostyril derivatives to interact with the β-adrenergic receptor was determined by competition assays. Reticulocyte membrane protein (0.003–0.008 mg) was incubated in a total volume of 0.15 ml containing 50 mM Tris.HCl buffer at pH 7.4, 30 pM of (−)-[$^{125}$I]-iodocyanopindolol, without (for controls) and with varying concentrations of ligands, 0.1 mM 5′-guanylyl imidodiphosphate (Gpp(NH)p) and without and with 0.001 mM alprenolol for 60 min at 36° C. At the end of the incubation, the suspensions were diluted with 4 ml of ice-cold incubation buffer and poured onto Whatman GF/B glass fiber filters under reduced pressure. Each filter was washed with a further 8 ml of ice-cold buffer, placed in a scintillation vial, and counted. Specific binding to the receptor was calculated as the difference between total binding determined in the absence of alprenolol and the nonspecific binding determined in the presence of alprenolol. Specific binding of [$^{125}$I]-iodocyanopindolol was about 95% of the total bound and was saturable with an apparent dissocation constant of 10 pM. The concentration of ligands that inhibited [$^{125}$I]iodocyanopindolol binding by 50% ($IC_{50}$) was determined from Hill plots. All data was statistically analyzed by using a one-way analysis of variance (ANOVA).

In the pretreatment experiments, reticulocyte membrane protein (3 mg/ml) was incubated in 50 mM Tris·HCl buffer at pH 7.4, containing 5 mM $MgCl_2$ without and with 20 nM compound 13 for 30 min at 32° C. A parallel incubation was also performed containing 20 nM compound 13 plus 10 μM nadolol. At the end of the incubation the tubes were filled (30 ml) with ice-cold incubation buffer and centrifuged at 48000 g for 15 min. The pellets were washed three more times by centrifugation and resuspension and the final pellets were resuspended in 1 ml of incubation buffer for assay. The membrane content of β-adrenergic receptors was determined with (-)-$^{125}$I]-iodocyanopindolol (10–100 pM) as described above. The binding maximums and dissociation constants ($K_D$) were determined from linear regression analysis of Scatchard plots.

Table 1 shows the ability of the three compounds set forth in FIG. 1 to inhibit [$^{125}$I]iodocyanopindolol (CYP) binding to the beta-adrenergic receptor and to stimulate adenylate cyclase activity in membranes prepared from rat reticulocytes. Comparisons are made to the classical beta-agonist (−)isoproterenol. The Table shows that the three compounds are 15- to 104-fold more potent than (−)isoproterenol for inhibiting CYP binding and 16- to 40-fold more potent for stimulating adenylate cyclase activity. In addition, compound (12) was equal to the intrinsic activity (efficacy) of (−)isoproterenol whereas compounds (11) and (13) have higher intrinsic activities than (−)isoproterenol. The data shows that all three compounds are highly potent beta-agonists with efficacies equal or higher than the catacholemine (−)isoproterenol. These compounds are stable in aqueous media as no reduction in potency or efficacy was observed when the compounds were re-used after several weeks at room temperature. Also, the high potency and efficacy of the iodo compound (structure 11) suggests that this compound synthesized with [$^{125}$I] would be useful for direct agonist-receptor interaction studies.

Figure 2:
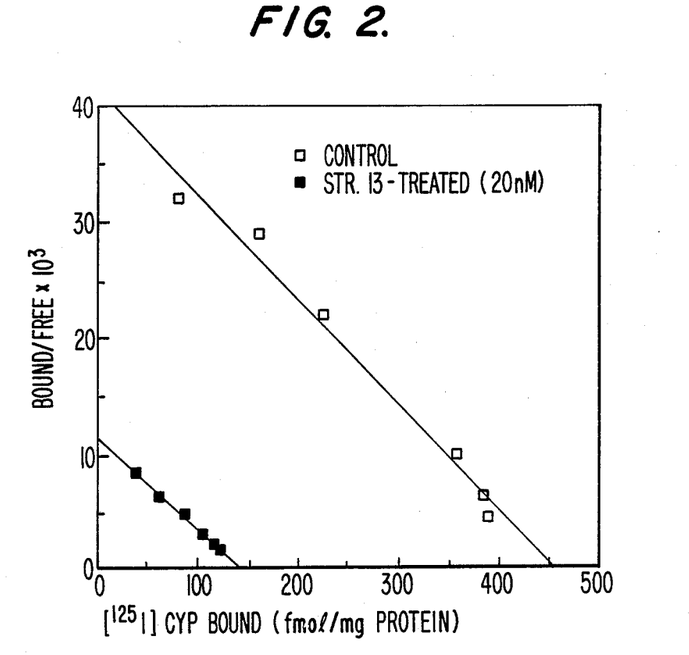

Irreversible binding of compound (13) to the reticulocyte β-adrenergic receptor was indicated by washout experiments. After membrane pretreatment with 20 nM of compound (13) followed by four wash cycles, there was a 71% decrease in the receptor concentration (control, 576±22; compound (13) treated, 168±15 fmol/mg of protein, mean ±SD, n=3) with no change in the $K_D$ value for (−)-[$^{125}$I]iodocyanopindolol binding to the remaining receptors (control 13±3; compound (13) treated, 11±2 pM). In addition, when nadolol (10 μM), a β-antagonist, was added to the preincubation in the presence of compound (13), the loss of specific binding sites was completely prevented. See FIG. 2.

Figure 3A:
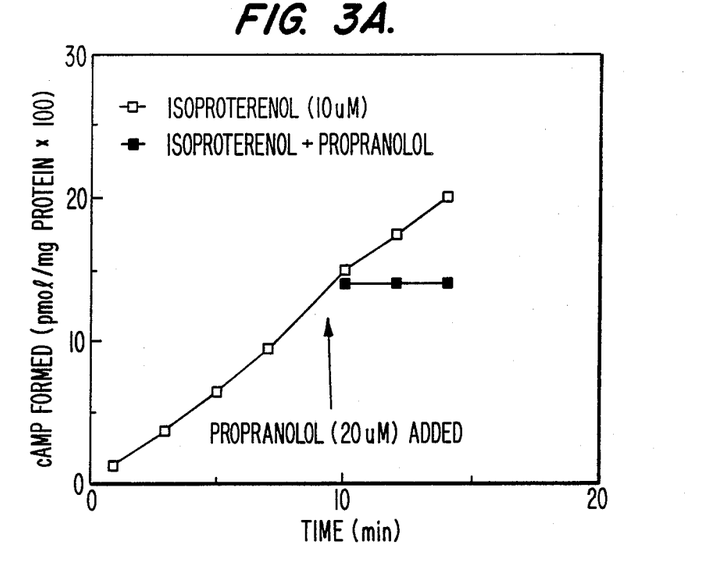
Figure 3B:
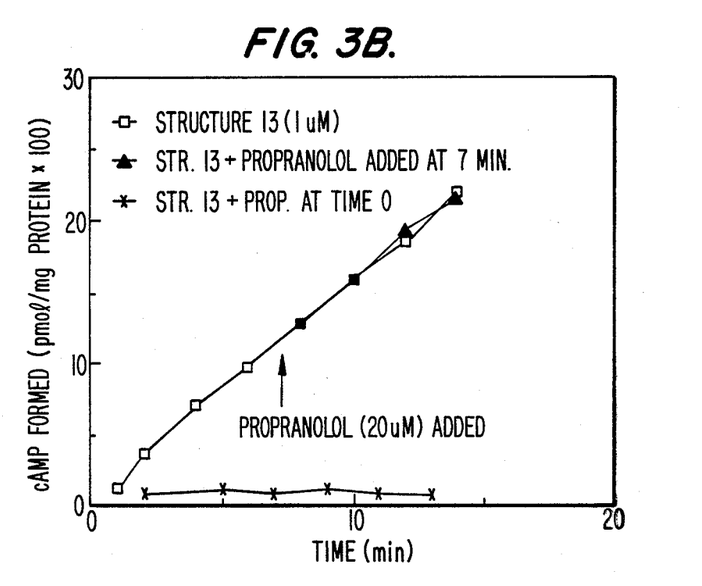

FIG. 3A shows the ability of (−)isoproterenol to stimulate adenylate cyclase activity in rat reticulocytes. Cyclic AMP production was linear through 14 min. When propranolol, a beta-antagonist, was added after 9 min of incubation, no further cAMP was produced. FIG. 3B, shows the same experimental protocol with structure (13). Similar to (−)isoproterenol, structure (13) stimulated cAMP production which was linear through 14 min. However, when propranolol was added after 7 min of incubation, no change in the rate of cAMP production occurred. In contrast, if propranolol was added with structure (13) at time O, then stimulation of cAMP production was blocked (FIG. 3B). The data indicates that once structure (13) binds to the receptor, it will not dissociate in the presence of an antagonist and continues to produce an agonist response. These data in conjunction with the binding data show that compound (13) irreversibly binds to the beta-adrenergic receptor and produces an irreversible response.

TABLE 1

Ability of (−)isoproterenol and carbostyril derivatives to stimulate adenylate cyclase activity and to inhibit [$^{125}$I] iodocyanopindolol (CYP) binding in rat reticulocyte membranes

| Ligand | Adenylate Cyclase | | CYP Binding |
|---|---|---|---|
| | $EC_{50}^a$ (nM) | Intrinsic Activity$^b$ | $IC_{50}^c$ (nM) |
| (1) Isoproterenol | 226 ± 1.4$^d$ | 1.0 | 327 ± 17 |
| 11 | 5.6 ± 1.4$^d$ | 1.3 | 7.6 ± 1.3$^d$ |
| 12 | 14.2 ± 4.7$^d$ | 1.0 | 22 ± 3$^d$ |
| 13 | 8.5 ± 3.5$^d$ | 1.2 | 5.3 ± 0.8$^d$ |

$^a$Concentration that produced half-maximal enzyme activation.
$^b$As compared to (−)isoproterenol which was set to 1.0.
$^c$Concentration that inhibited CYP binding by 50%.
$^d$Significantly different from the (−)isoproterenol group (P < 0.001) by ANOVA.
All data is the mean ±SE, n = 3-6.

Table 2 shows the ability of structure (13) to induce a receptor loss in various rat tissues. Rats were injected i.p. with either 2 or 5 mg/kg of structure (13) and 3 hr. later, the tissues were removed and assayed for the beta-adrenergic receptor content.

TABLE 2

Structure 13 induced loss of beta-adrenergic receptors in various tissues of the rat.

| | Specific Ligand Binding (fmol/mg protein) | | |
|---|---|---|---|
| | | Compound 13-dose | |
| Tissue | Control | 2 mg/kg | 5 mg/kg |
| Lung | 658 ± 27 | 318 ± 23 (52) | 166 ± 9 (75) |
| Spleen | 53.2 ± 1.8 | 31 ± 4 (42) | 19 ± 1.2 (65) |
| Heart | 22.3 ± 1.0 | 17.1 ± 0.5 (23) | 18.9 ± 0.8 (15) |
| Submaxillary gland | 98 ± 5.8 | 75 ± 3 (23) | 77 ± 3.7 (21) |
| Cerebral cortex | 119 ± 10 | — | 114 ± 14 |

Each number is the mean ±S.E., N = 8-12. Numbers in parenthesis is the % reduction from controls.

The data shown that 3 hours after a 2 mg/kg injection of compound (13) there was a 52, 42, 23 and 23% loss of beta-adrenergic receptors in the lung, spleen, heart and submaxillary gland respectively. When the dose of compound (13) was increased to 5 mg/kg, the loss of receptors was increased to 75% in the lung and to 65% in the spleen. In contrast, no further loss of receptors was detected in the heart or submaxillary gland at the higher dose given. There was no significant loss of receptors in the cerebral cortex after treatment with compound (13) at 5 mg/kg. The ratio of beta-1 to beta-2 adrenergic receptors in these tissues is lung, 22:78; spleen, 17:83; heart, 70:30; submaxillary gland, 85:15 and brain, 65:35.

The much greater loss of receptors in the lung and spleen which have a majority of beta-2 receptors indicates that the receptor reductions were mainly due to losses of beta-2 receptors. This is further supported by the relatively small loss of receptors in the heart and submaxillary gland which mainly contains beta-1 receptors. Finally, the lack of any receptor loss in the cerebral cortex suggests that the compound cannot cross the blood brain barrier and penetrate the central nervous system.

Table 3 shows the ability of structure (13) and (−)isoproterenol to produce a beta-adrenergic receptor mediated response in the rat lung. Rats were injected (i.p.) with the classical beta-agonist (−)isoproterenol (0.1 mg/kg) or compound (13) (0.1 mg/kg) and 3 hours later the lungs were removed and assayed for the induction of the enzyme, ornithine decarboxylase. To show that any effect was due to beta-adrenergic receptor stimulation, propranolol (5 mg/kg), the classical beta-antagonist was given to some animals 30 min. before the injection of isoproterenol or compound (13). The data show that (−)isoproterenol and compound (13) induced ornithine decarboxylase activity by 6.5 and 4.6 fold respectively and that this induction was completely blocked by propranolol.

TABLE 3

Structure 13 and (−)isoproterenol effects on ornithine decarboxylase activity in the rat lung

| Treatment | Ornithine decarboxylase activity (nmol $CO_2$ Formed/g tissue/hr) |
|---|---|
| Basal (control) activity | 1.9 + 0.4 |
| (−)Isoproterenol (0.1 mg/kg) | 11.8 + 1.7 (6.2) |
| (−)Isoproterenol (0.1 mg/kg) plus propranolol (5 mg/kg) | 0.4 + 0.09 |
| Compound 13 (0.1 mg/kg) | 8.7 + 0.5 (4.6) |
| Compound 13 (0.1 mg/kg) plus propranolol (5 mg/kg) | 0.4 + 0.06 |

Each number is the mean +S.E., N = 5.6. Numbers in parenthesis is the Fold increase over the basal level.

These results show that compound (13) produces a stimulatory effect in vivo which is mediated through the beta-adrenergic receptor.

A simplified procedure can be used to convert the amine cogener (structure 12) to the radiolabeled [$^{125}$I]-cogener (structure 13) for use in direct assay procedures. This general triazene decomposition method has been described previously (Van Dort et al, J. Med. Chem., Vol. 30, pp. 1241-1244 (1987)]. The reaction scheme is:

where R—NH$_2$ is structure 12 and R—[$^{125}$I] is structure 13 with the nonradioactive iodine replaced with radioactive iodine ($^{125}$I). Reaction (1) is performed by sequential treatment with nitrous acid followed by alkaline pyrrolidine. Reaction (2) is carried out with trifluoroacetic acid and sodium iodide (Na $^{125}$I).

We claim:
1. A compound having beta-adrenergic receptor agonist properties having the formula:

wherein X may be the ortho, meta or para position and is selected from the group consisting of halogen, amino and substituted and unsubstituted lower alkanoylamino having from 1 to 6 carbon atoms wherein said substituents are pharmaceutically acceptable and pharmaceutically acceptable salts and complexes thereof.

2. A compound according to claim 1 wherein X is NH$_2$.

3. A compound, salt or complex according to claim 1 labeled with an assayable ligand.

4. In a method of measuring beta-adrenergic receptors comprising exposing said receptors to a beta-adrenergic agonist and assaying the extent of interaction therebetween, the improvement comprising exposing said receptors to a compound, salt or complex of claim 1 labelled with an assayable ligand.

5. A pharmaceutical composition in unit dosage form adapted for measuring beta-adrenergic receptors comprising an amount of a compound, salt or complex of claim 1 labelled with an assayable ligand sufficient to assyably interact with said beta-adrenergic receptors and a pharmaceutically acceptable carrier therefor.

6. A compound to claim 1 wherein X is I.

7. A compound according to claim 6 wherein X is NHCOCH$_2$Br.

8. A salt of a compound according to claim 1 wherein said salt is selected from the group consisting of hydrohalides, acetate, maleate, benzoate, hemisulfate, fumarate and oxalate.

9. A salt according to claim 8 wherein said hydrohalide is hydrochloride or hydrobromide.

* * * * *

UNITED STATES PATENT AND TRADEMARK OFFICE
CERTIFICATE OF CORRECTION

PATENT NO. : 4,894,219

DATED : January 16, 1990

INVENTOR(S) : Stephen P. BAKER ET AL

It is certified that error appears in the above-identified patent and that said Letters Patent is hereby corrected as shown below:

In Claim 5, line 5: "assyably" should read -- assayably --.

Signed and Sealed this

Twelfth Day of February, 1991

*Attest:*

HARRY F. MANBECK, JR.

*Attesting Officer*      *Commissioner of Patents and Trademarks*